Figure 1:
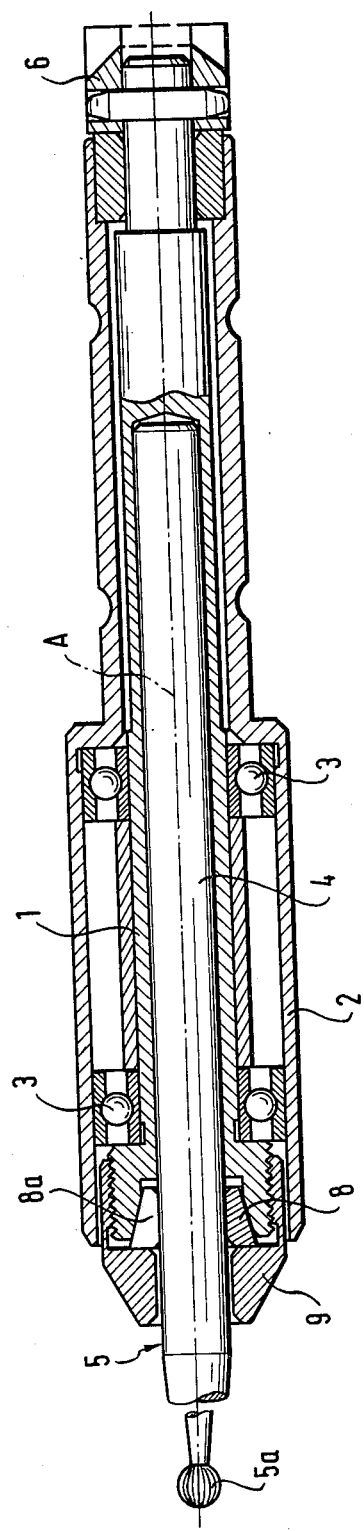

United States Patent [19]

Loge

[11] 3,994,070
[45] Nov. 30, 1976

[54] CONNECTOR FOR DENTAL TOOLS

[75] Inventor: Hans Loge, Biberach an der Riss, Germany

[73] Assignee: Kaltenbach & Voigt, Biberach an der Riss, Germany

[22] Filed: Oct. 11, 1974

[21] Appl. No.: 514,323

[30] Foreign Application Priority Data

Oct. 19, 1973 Germany............................ 2352645

[52] U.S. Cl. ............................................... 32/27
[51] Int. Cl.² .......................................... A61C 1/10
[58] Field of Search ................. 32/26, 27; 279/1 A, 279/15 G, 58, 1 Q

[56] References Cited
UNITED STATES PATENTS

| | | | |
|---|---|---|---|
| 1,056,341 | 3/1913 | Keltie.................................... | 32/27 |
| 2,880,007 | 3/1959 | Stoner.................................. | 279/1 Q |
| 3,314,153 | 4/1967 | Maurer................................. | 32/27 |
| 3,324,553 | 6/1967 | Borden................................ | 279/1 Q |

*Primary Examiner*—Robert Peshock
*Attorney, Agent, or Firm*—Haseltine, Lake & Waters

[57] ABSTRACT

Connector for rotary dental tools and the like, comprising a housing, a support sleeve rotatably journaled in the housing to receive a shaft of a dental tool, wherein the sleeve is in the form of a circumferentially closed tubular member that surrounds the shaft without any play, and clamping means between the sleeve and the shaft, for immobilizing the tool prior to imparting rotary movement thereto, the clamping means being elastically deformable in the radial direction, and short in comparison to the length of the sleeve. Two exemplary embodiments are disclosed, one including a mechanism that includes a follower and a clamping nut for the tool, while the other has an inner turbine wheel and a conical support ring with a collar and a biasing spring acting on the clamping means.

5 Claims, 2 Drawing Figures

CONNECTOR FOR DENTAL TOOLS

The present invention relates to a connector for dental instruments or tools, consisting of a support sleeve which receives the tool shaft and is supported so as to be rotatable in a housing about its longitudinal axis, and which is connectable with the tool shaft for the purpose of transmitting rotational movement to the tool.

Such a connector for dental tools is known from Swiss Pat. No. 381,802. In that instance, a support sleeve is formed as a connecting clamp which is slotted along its entire length, and which can be inserted in a driving sleeve that forms the housing. After the insertion of the tool into the clamp, the latter does not touch the inner wall of the housing with the long area of its longitudinal slots, which is also caused by the clamp becoming deformed during the clamping operation so that the tool shaft in the mentioned areas does not have any guidance from the support sleeve. The result thereof is eccentric running and knocking in the tool, which results in inaccuracies during dental operations, and also in surgical drilling, cutting and boring work. There is also caused a rapid wear of the support.

The same is also applicable to a connecting arrangement known from German Pat. No. 1,566,241, in which similarly there is provided a support sleeve shaped as a longitudinally slotted clamping member in a housing, which does not rotate therewith.

Accordingly, it is an object of the present invention to provide a clamping arrangement or connector of the above-mentioned type in which eccentric running of the tool is avoided.

In order to solve the foregoing object, it is proposed in the present invention that the support sleeve be constructed as a circumferentially closed tubular member which encompasses the tool shaft in a tolerance-free manner so that, for the connection between the shaft and the guide sleeve, there is located a clamping ring which is elastically deformable in a radial direction and that is short relative to the length of the support sleeve.

It is achieved hereby that the clamping effect is exerted only in the region of the relatively short clamping ring so that the tool shaft is journaled in the support sleeve snugly and without any play, namely with the remaining length thereof that is within the sleeve, due to the lack of longitudinal slots. This eliminates any knocking and/or untrue running of the tool. The dentist or surgeon can thus operate more precisely, and additionally wear of the journaling is held as small as possible due to the afforded concentric running thereof.

It has been found that the arrangement of the clamping ring at one end of the support sleeve is advisable.

A further embodiment of the inventive dental-tool connector is characterized in that the outer wall of the clamping ring is conically shaped and lies against a correspondingly conically shaped part of the inner wall of the sleeve. If upon sliding in of the tool the clamping ring is axially moved, then the clamping effect is achieved as a result of the conical elements according to the invention. A clamping nut may also be provided that is externally actuatable. Furthermore the invention recommends the use of a pre-tensioned spring that is effective on the clamping ring in the axial direction.

Preferably the clamping ring is slotted so as to endure elastic deformation in a radial direction. It is however also possible to construct the clamping ring from an appropriate elastic material, which would render unnecessary to provide a slot.

According to major features of the invention, a connector for dental tools is provided which comprises a housing, a support sleeve rotatably journaled in the housing to receive the shaft of a dental tool and the like, wherein the sleeve is in the form of a circumferentially closed tubular member that surrounds the shaft without any play, and clamping means between the sleeve and the shaft, preferably in the form of a ring, for immobilizing the tool prior to imparting rotary movement thereto, the means being elastically deformable in the radial direction, and short in comparison to the length of the sleeve.

The ring-shaped clamping means is preferably disposed in the proximity of one of the ends of the support sleeve, namely at the tool end. The ring-shaped clamping means may have a conically shaped outer wall in contact with a similarly conically shaped inner wall portion of the support sleeve.

As mentioned before, the clamping means (ring) may have at least one slot therein, or be made from an elastic material, without the need for a slot.

According to further, optional features of the invention, one of the exemplary embodiments may include a follower adjacent one end of the support sleeve for imparting the rotary movement to the tool, and an adjustable clamping nut that surrounds an outer end portion of the shaft, allowing the tool to be selectively immobilized in and released from the connector.

In another exemplary embodiment, the support sleeve has a collar portion while another portion thereof is formed as a turbine wheel, the connector further comprising an adjustable support ring that surrounds an outer end portion of the tool shaft in end-to-end relation to the clamping means, the support ring having an inwardly directed conical portion, and a spring resting on the collar portion for outwardly biasing the support ring.

Figure 2:
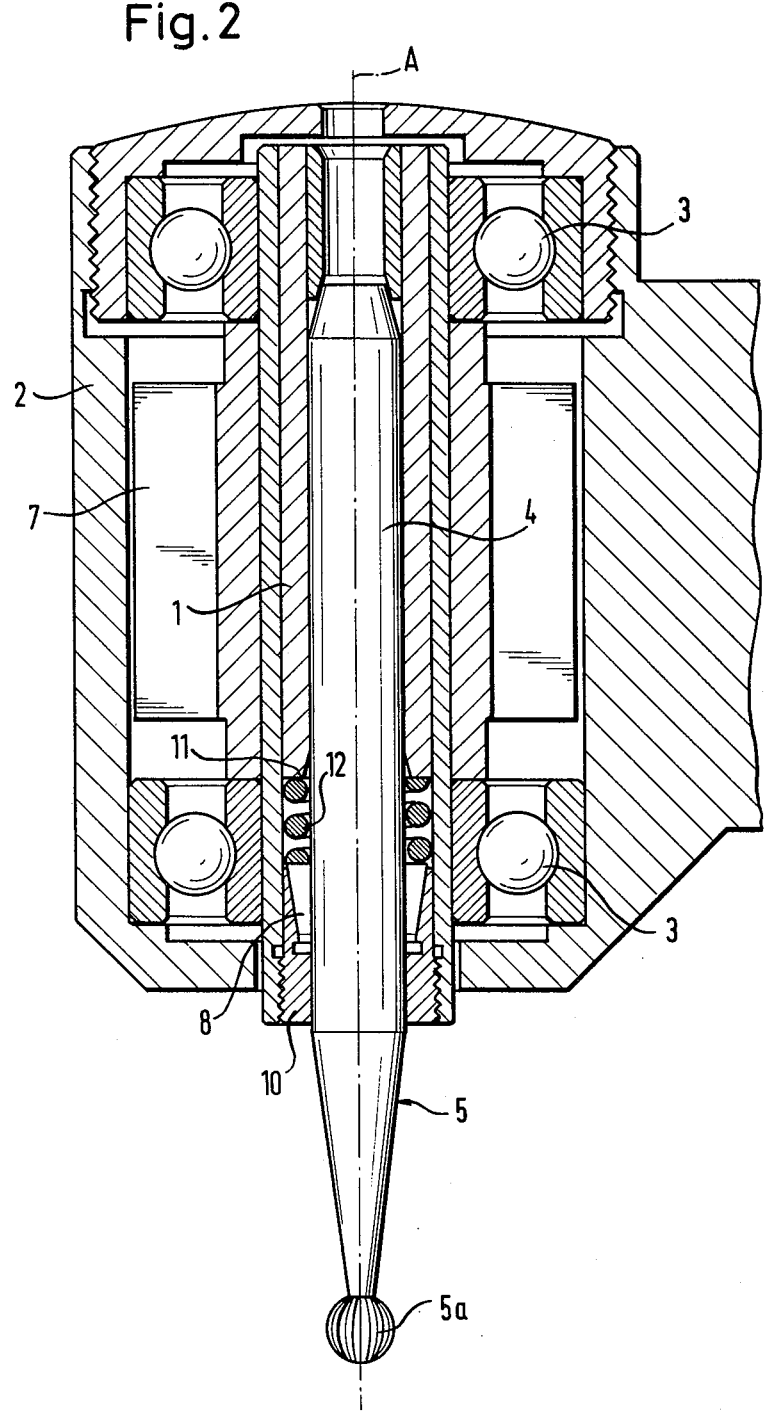

The inventive connector for dental tools will now be described in full detail, together with its characteristic features, operation and the inherent advantages thereof, by reference to the accompanying drawings wherein FIG. 1 shows a connector according to the invention with a tool inserted, suitable for a straight-line dental or surgical handpiece, in a longitudinal section; and FIG. 2 is a slightly modified embodiment of an angularly constructed handpiece, also in a longitudinal section.

In both embodiments, namely those shown in FIGS. 1 and 2, a support sleeve 1 is rotatable about its longitudinal axis A and supported in a housing 2 by means of ball bearings 3 and the like. The sleeve 1 is constructed as a tubular member closed about its entire circumference, which closely hugs a shaft 4 of a tool generally designated with numberal 5 which, in the present instance, is shown as a dental drill. No play is allowed between the tubular support sleeve member 1 and the tool 5.

In the embodiment of FIG. 1, the sleeve 1 is imparted rotation by means of a follower 6 located at its right-hand or rear end.

In the modified embodiment of FIG. 2, the sleeve 1 is constructed of two rotationally interconnected coaxial sleeves and has a turbine wheel or runner 7 thereon.

For transmission of the rotational movement of the sleeve 1 to the tool 5, the former is connectable in both embodiments with the shaft 4. To this end, there is provided a clamping ring 8 between the sleeve 1 and the shaft 4, which ring is much shorter than the support sleeve, and which is deformable in a radial direction. The clamping ring 8, constituting clamping means, is provided at the end of the sleeve 1 that faces toward a tip 5a of the tool 5.

In FIG. 2, the clamping ring could also be disposed at the other or rear end of the support sleeve 1.

As shown in the drawing, the outer wall of the clamping ring 8 is conically shaped. With this conical wall the ring 8 lies against or contacts a correspondingly conically shaped portion of the inner wall of the sleeve 1.

FIG. 1 shows that the clamping ring 8 may be provided with at least one slot 8a, to allow elastic deformation in the radial direction.

In FIG. 1, clamping is effected by sliding or pushing the tool shaft 4 into the sleeve 1 after clamping nut 9 has been turned outwardly with its threads, the nut being located at the forward end of the sleeve 1, facing toward the tip 5a of the tool, until the ring 8 is opened to facilitate insertion. After completely sliding in the tool shaft 4 into sleeve 1, the latter being tubularly formed along its entire length, the nut 9 is tightened whereupon the clamping ring 8 is radially inwardly deformed as a result of the earlier mentioned conical walls.

In the alternative or modified embodiment of FIG. 2, a support ring 10 is threaded into the end of the sleeve 1 that faces the tool tip 5a, the ring 10 contacting the clamping ring 8. One end of the ring 10 forms a conically shaped portion of the inner wall of the support sleeve 1. Between the ring 8 and an annular collar 11 of the sleeve 1 there is located a spiral spring 12 which urges the ring 8 into the clamping position, that is toward the ring 10 or the tool tip 5a.

Upon having slid the tool 5 into the sleeve 1, the shaft 4 pushes against the clamping ring 8 and thereby compresses the spring 12. This temporarily removes the contact between the two conically engaging ring portions 8 and 10, so that the clamping ring 8 may be outwardly elastically unloaded, in the radial direction, so that the shaft 4 can be pushed into the support sleeve 1, through the ring 8. After the insertion is completed, the spring 12 becomes effective, returning the ring 8 into engagement with the conical walls so that the ring 8 exerts its clamping effect. The support ring 10 has a threaded outer surface by which it is adjustable within the connector body so that the pre-tensioning of the spring 12 can be altered.

It will be understood that several modifications in and additions to the described and illustrated preferred exemplary embodiments of the inventive connector can be made without departing from the spirit and scope of the invention.

What is claimed is:

1. A connector for dental tools and the like, comprising: a housing; a support sleeve rotatably journaled in said housing to receive the shaft of a dental tool; wherein said sleeve is in the form of a circumferentially closed tubular member that surrounds the tool shaft substantially along its entire length without any play; said sleeve having an inner diameter in the area of one of its ends that is larger than its inner diameter in other areas thereof; and a single-piece clamping ring located between said sleeve and the tool shaft in said area of larger diameter, for immobilizing the tool prior to imparting rotary movement thereto; said clamping ring being elastically deformable in the radial direction, and being short in comparison with the length of said sleeve.

2. The connector as defined in claim 1, wherein said support sleeve has a collar portion and another portion thereof formed as a turbine wheel; and further comprising an adjustable support ring surrounding an outer end portion of the tool shaft in end-to-end relation to said clamping ring; the latter having an inwardly directed conical portion; and spring means resting on said cover portion for outwardly biasing said clamping ring.

3. The connector as defined in claim 1, wherein said clamping ring has a conically shaped outer wall in contact with a similarly conically shaped inner wall portion of said support sleeve.

4. The connector as defined in claim 1, wherein said clamping ring has at least one slot therein.

5. The connector as defined in claim 1, further comprising a follower adjacent one end of said support sleeve for imparting the rotary movement to the tool, and an adjustable clamping nut surrounding an outer end portion of the tool shaft located at the forward end of said sleeve and facing towards the tip of the tool for allowing the tool to be selectively immobilized in and released from the connector.

* * * * *